(12) United States Patent
Wilson

(10) Patent No.: US 7,939,096 B2
(45) Date of Patent: May 10, 2011

(54) MEDICAL IMPLANTS WITH POLYSACCHARIDE DRUG ELUTING COATINGS

(75) Inventor: Geoffrey Wilson, Mahtomedi, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 12/369,397

(22) Filed: Feb. 11, 2009

(65) Prior Publication Data

US 2009/0202610 A1  Aug. 13, 2009

Related U.S. Application Data

(60) Provisional application No. 61/027,981, filed on Feb. 12, 2008.

(51) Int. Cl.
*A61L 27/54* (2006.01)
(52) U.S. Cl. ........................ 424/426; 427/2.25
(58) Field of Classification Search .................. None
See application file for complete search history.

(56) References Cited

U.S. PATENT DOCUMENTS

| | | | |
|---|---|---|---|
| 5,195,969 A | 3/1993 | Wang et al. | |
| 5,270,086 A | 12/1993 | Hamlin | |
| 5,478,355 A * | 12/1995 | Muth et al. | 606/230 |
| 5,733,925 A | 3/1998 | Kunz et al. | |
| 5,893,839 A * | 4/1999 | Johnson | 604/506 |
| 6,726,712 B1 | 4/2004 | Raeder-Devens et al. | |
| 2003/0149475 A1* | 8/2003 | Hyodoh et al. | 623/1.19 |
| 2003/0175327 A1* | 9/2003 | Cochrum et al. | 424/445 |
| 2005/0025804 A1* | 2/2005 | Heller | 424/423 |
| 2005/0163821 A1* | 7/2005 | Sung et al. | 424/426 |
| 2005/0261760 A1 | 11/2005 | Weber | |
| 2005/0283229 A1* | 12/2005 | Dugan et al. | 623/1.38 |
| 2006/0271168 A1 | 11/2006 | Kleine et al. | |
| 2006/0286141 A1 | 12/2006 | Campbell | |
| 2007/0254041 A1 | 11/2007 | Drapeau et al. | |
| 2007/0288085 A1 | 12/2007 | Furst | |

FOREIGN PATENT DOCUMENTS

| | | |
|---|---|---|
| WO | WO 97/39737 | 10/1997 |
| WO | WO 2008/092435 | 8/2008 |

OTHER PUBLICATIONS

Yeung "Biocompatible and Absorbable Coating and Stents". http://www.j-circ.or.jp/english/sessions/reports/69th/sym04.htm.*
Authorized officer Patrick Wach, International Search Report/Written Opinion in PCT/US09/33792 mailed May 3, 2010, 12 pages.

* cited by examiner

*Primary Examiner* — Robert A Wax
*Assistant Examiner* — Danah Al-Awadi
(74) *Attorney, Agent, or Firm* — Fish & Richardson P.C.

(57) ABSTRACT

A medical implant can include a bioerodible metal portion and a coating overlying the bioerodible metal portion. The coating can include a therapeutic agent and a polysaccharide matrix reversibly cross-linked with polyvalent metal cations. Upon implantation of the implant within a body, the therapeutic agent is released and the bioerodible metal portion erodes to release polyvalent metal cations capable of re-cross-linking the polysaccharide matrix.

12 Claims, 1 Drawing Sheet

MEDICAL IMPLANTS WITH POLYSACCHARIDE DRUG ELUTING COATINGS

CROSS-REFERENCE TO RELATED APPLICATIONS

This application claims priority under 35 USC §119(e) to U.S. Provisional Patent Application Ser. No. 61/027,981, filed on Feb. 12, 2008, the entire contents of which are hereby incorporated by reference.

TECHNICAL FIELD

This invention relates to medical implants, and more particularly to stents.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Examples of endoprostheses include stents, covered stents, and stent-grafts.

Endoprostheses can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

The expansion mechanism can include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn.

In another delivery technique, the endoprosthesis is formed of an elastic material that can be reversibly compacted and expanded, e.g., elastically or through a material phase transition. During introduction into the body, the endoprosthesis is restrained in a compacted condition. Upon reaching the desired implantation site, the restraint is removed, for example, by retracting a restraining device such as an outer sheath, enabling the endoprosthesis to self-expand by its own internal elastic restoring force.

The endoprosthesis can carry a drug, such as an antiproliferative, to reduce the likelihood of restenosis, i.e., reclosure of the vessel due to immune reactions by the body at the treatment site.

SUMMARY

A medical implant is described that includes a bioerodible metal portion and a coating overlying the bioerodible metal portion. The coating can include a therapeutic agent and a polysaccharide matrix reversibly cross-linked with polyvalent metal cations. Upon implantation of the implant within a body, the therapeutic agent is released and the bioerodible metal portion erodes to release polyvalent metal cations capable of re-cross-linking the polysaccharide matrix.

In some embodiments, the polyvalent metal cations of the coating can be the same element as the polyvalent metal cations released by the bioerodible metal portion upon implantation. The cations of the coating can be oxides, hydroxides, or salts of elements selected from Groups IIA, IIIB, IVB, VB, VIB, VIIB, VIIIB, IB, and IIB of the periodic table. Additionally, the cations of the coating can be oxides, hydroxides, or salts of Al, Ga, In, Sn, Tl, or Bi. For example, polyvalent metal cations of the coating can be $Mg^{2+}$, $Zn^{2+}$, $Ca^{2+}$, $Ba^{2+}$, $Fe^{2+}$, $Fe^{3+}$, $Al^{3+}$, $Bi^{4+}$, or a combination thereof. The cation can also be a molecule capable of cationic bonding. In some embodiments, the coating can include a plurality of different cations. In some embodiments, the polyvalent cations in the matrix can have a valence of 3 or greater.

In some embodiments, the polysaccharide can be alginate, agar, gum Arabic, xanthan gum, dextran, gellan gum, pullulan, or combinations thereof.

In some embodiments, the bioerodible metal portion can include a metal selected from the group consisting of magnesium, iron, zinc, and alloys thereof. In some embodiments, the bioerodible metal portion can include an oxide, hydroxide, or salt of one or more of the following elements: Mg, Ca, Ba, Sr, Fe, Fe, Al, and Bi (e.g., MgO or $FeCl_3$).

In some embodiments, the medical implant can be a stent.

A method of forming the medical implant is also described. The method can include applying an aqueous dispersion or solution of a therapeutic agent and a polysaccharide to a surface of a medical implant to produce a coating overlying a bioerodible metal portion of the implant. In some embodiments, the method can further include oxidizing the surface of the medical implant. In some embodiments, the aqueous dispersion or solution can include an oxidation accelerant. For example, metal chloride salts and peroxides can be used as oxidation accelerants. In some embodiments, a precursor of the medical implant can include a metal selected from Groups IIA, IIIB, IVB, VB, VIB, VIIB, VIIIB, IB, IIB of the periodic table, Al, Ga, In, Sn, Tl, Bi, and combinations thereof.

The details of one or more embodiments are set forth in the accompanying drawings and the description below. Other features, objects, and advantages will be apparent from the description and drawings, and from the claims.

DESCRIPTION OF DRAWINGS

Like reference symbols in the various drawings indicate like elements.

DETAILED DESCRIPTION

A medical implant can replace, support, or act as a missing biological structure. Some examples of medical implants can include orthopedic implants; endoprostheses such as stents, covered stents, and stent-grafts; bone screws; aneurism coils. Medical implants can include a bioerodible metal portion and a coating overlying the bioerodible metal portion. The coating can include a therapeutic agent and a polysaccharide matrix reversibly cross-linked with polyvalent metal cations. Upon implantation of the implant within a body, the matrix hydrates and solubilizes, thereby releasing the therapeutic agent, and the bioerodible metal portion erodes to release polyvalent metal cations capable of re-cross-linking the polysaccharide matrix. As described below, the release of polyvalent metal cations from the bioerodible metal portions can regulate the rate of hydration and solubilization of the polysaccharide matrix and therefore can regulate the release of the therapeutic agent. Although equally applicable to other medical implants, the following discussion will refer to a stent having a bioerodable metal portion and a coating including a therapeutic agent and a polysaccharide matrix.

Figure 1:
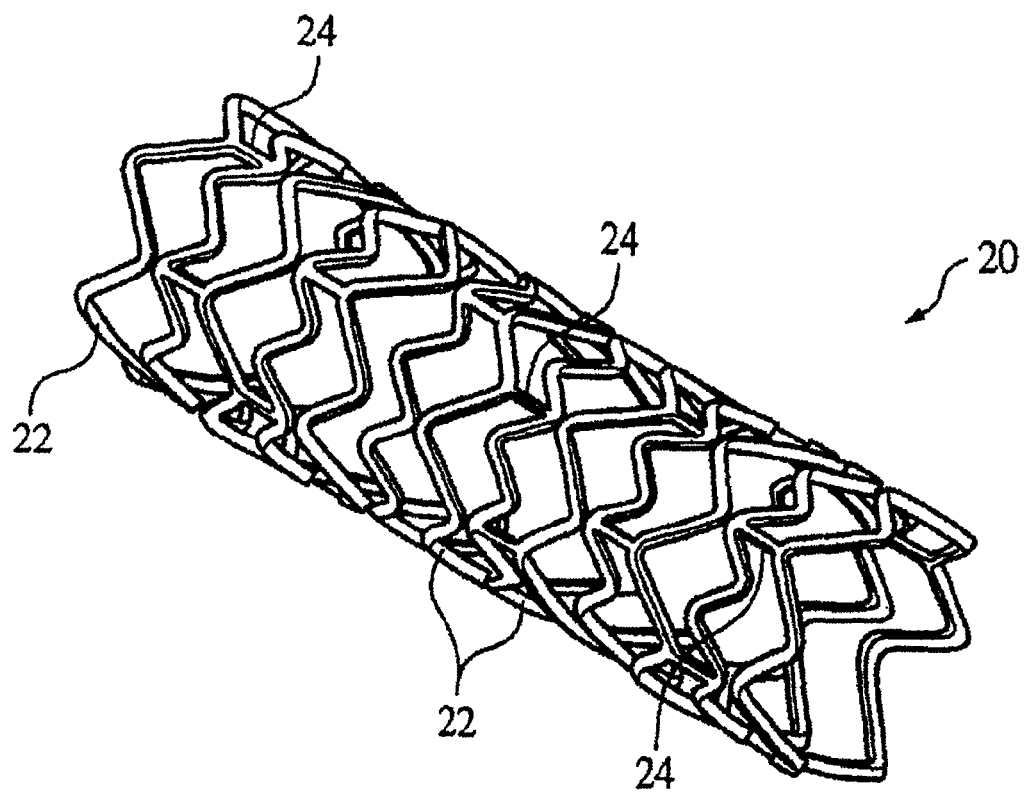
FIG. 1 is a perspective view of an example of an expanded stent.

Referring to FIG. 1, stent 20 can have the form of a tubular member defined by a plurality of bands 22 and a plurality of connectors 24 that extend between and connect adjacent bands. During use, bands 22 can be expanded from an initial, small diameter to a larger diameter to contact stent 20 against a wall of a vessel, thereby maintaining the patency of the vessel. Connectors 24 can provide stent 20 with flexibility and conformability that allow the stent to adapt to the contours of the vessel.

Figure 2A:
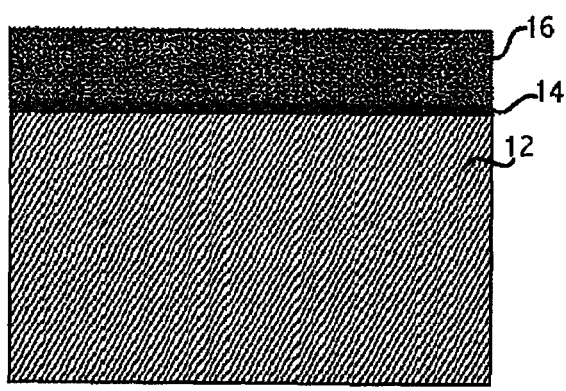
FIGS. 2A and 2B depict a process of applying a coating including a therapeutic agent and a polysaccharide matrix.
Figure 2B:
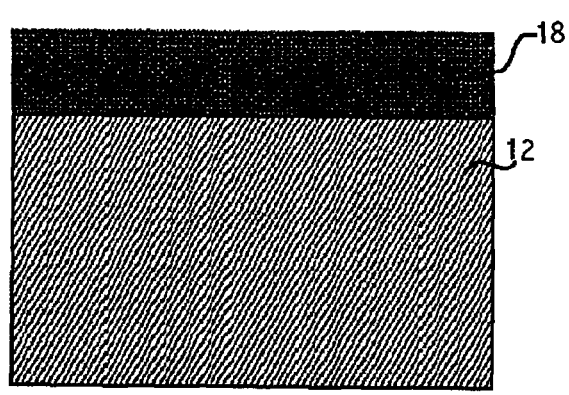

As shown in FIG. 2B, stent 20 can include a bioerodible metal portion 12 and a coating 18 overlying the bioerodible metal portion 12. The coating can include a therapeutic agent and a polysaccharide matrix reversibly cross-linked with polyvalent metal cations. For example, the coating could include alginate cross-linked with $Mg^{+2}$ cations. The therapeutic agent can be dispersed within the polysaccharide matrix. The polysaccharide in the polysaccharide matrix can be any branched or unbranched polysaccharide. Examples of suitable polysaccharides include alginate, agar, gum arabic, xanthan gum, dextran, gellan gum, pullulan, and combinations thereof.

The presence of the polyvalent cation within the coating 18 can render the polysaccharide matrix insoluble. Examples of polyvalent metal cations can include $Mg^{2+}$, $Zn^{2+}$, $Ca^{2+}$, $Ba^{2+}$, $Fe^{2+}$, $Fe^{3+}$, $Al^{3+}$, $Bi^{4+}$, and combinations thereof. In some embodiments, the polyvalent cations in the matrix can have a valence of 3 or greater. The polyvalent metal cations of the coating can be the same element as the polyvalent metal cations released by the bioerodible metal portion upon implantation of the stent.

The bioerodible metal portion 12 can include any bioerodible metal. For example, the bioerodible metal can be magnesium, iron, zinc, or alloys thereof. In some embodiments, the bioerodible metal can erode upon implantation such that one or more elements of the bioerodible metal are released as polyvalent cations. For example, magnesium in a bioerodible magnesium alloy can erode to produce $Mg^{2+}$. In some embodiments, the bioerodible metal portion can include an alloy including a first element selected from Mg, Ca, Ba, Al, Bi, and combinations thereof and the bioerodible metal can erode to release the first element as a polyvalent metal cation upon implantation. In some embodiments, the bioerodible metal portion can include oxides or salts that can ionize under physiological conditions to release polyvalent metal cations. For example, the oxide or salt can be an oxide or salt of Mg, Ca, Ba, Fe, Al, or Bi (e.g., MgO or $FeCl_3$). In some embodiments, the bioerodible metal portion can include deposits of the oxides or salts within a matrix of the bioerodible metal.

The therapeutic agent can be dispersed within the polysaccharide matrix. The terms "therapeutic agent", "pharmaceutically active agent", "pharmaceutically active material", "pharmaceutically active ingredient", "drug" and other related terms may be used interchangeably herein and include, but are not limited to, small organic molecules, peptides, oligopeptides, proteins, nucleic acids, oligonucleotides, genetic therapeutic agents, non-genetic therapeutic agents, vectors for delivery of genetic therapeutic agents, cells, and therapeutic agents identified as candidates for vascular treatment regimens, for example, as agents that reduce or inhibit restenosis. By small organic molecule is meant an organic molecule having 50 or fewer carbon atoms, and fewer than 100 non-hydrogen atoms in total.

Exemplary non-genetic therapeutic agents for use in conjunction with the presently disclosed endoprostheses an include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) anti-neoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick anti-platelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) alpha receptor antagonist (such as doxazosin, Tamsulosin) and beta receptor agonists (such as dobutamine, salmeterol), beta receptor antagonist (such as atenolol, metaprolol, butoxamine), angiotensin-II receptor antagonists (such as losartan, valsartan, irbesartan, candesartan and telmisartan), and antispasmodic drugs (such as oxybutynin chloride, flavoxate, tolterodine, hyoscyamine sulfate, diclomine), (u) bARKct inhibitors, (v) phospholamban inhibitors, (w) Serca 2 gene/protein, (x) immune response modifiers including aminoquizolines, for instance, imidazoquinolines such as resiquimod and imiquimod, and (y) human apolioproteins (e.g., AI, AII, AIII, AIV, AV, etc.).

Specific examples of non-genetic therapeutic agents include paclitaxel, (including particulate forms thereof, for instance, protein-bound paclitaxel particles such as albumin-bound paclitaxel nanoparticles, e.g., ABRAXANE), sirolimus, everolimus, tacrolimus, zotarolimus, picrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well a derivatives of the forgoing, among others.

Exemplary genetic therapeutic agents for use in conjunction with the presently disclosed endoprostheses include anti-sense DNA and RNA as well as DNA coding for the various proteins (as well as the proteins themselves): (a) anti-sense RNA, (b) tRNA or rRNA to replace defective or deficient endogenous molecules, (c) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers PVP, SP1017 (SUPRATEK), lipids such as cationic lipids, liposomes, lipoplexes, nanoparticles, or microparticles, with and without targeting sequences such as the protein transduction domain (PTD).

Cells for use in conjunction with the presently disclosed endoprostheses include cells of human origin (autologous or allogeneic), including whole bone marrow, bone marrow derived mono-nuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the presently disclosed endoprostheses and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin, macrolide antibiotics such as erythromycin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline. Further additional therapeutic agents for the presently disclosed endoprostheses are also disclosed in U.S. Pat. No. 5,733,925.

Where a therapeutic agent is included, a wide range of therapeutic agent loadings can be used in conjunction with the presently disclosed endoprostheses, with the therapeutically effective amount being readily determined by those of ordinary skill in the art and ultimately depending, for example, upon the condition to be treated, the age, sex and condition of the patient, the nature of the therapeutic agent, the nature of the ceramic region(s), and/or the nature of the endoprosthesis, among other factors. The delivery mediated is formulated as needed to maintain cell function and viability.

In some embodiments, the stent can also include a non-bioerodible portion. For example, a stent could include bands and/or connectors of stainless steel with a layer of magnesium and an overcoating including alginate and a therapeutic agent.

The coating can be formed on a stent by applying an aqueous dispersion or solution of a therapeutic agent and a polysaccharide to a surface of a stent that is capable of releasing polyvalent metal cations. The aqueous dispersion or solution can include soluble polysaccharide anions, acids, or salts. For example, the aqueous dispersion or solution can be created by adding a soluble salt of a polysaccharide (e.g., sodium alginate) to water. Accordingly, in some embodiments, the aqueous dispersion or solution and the resulting coating can include monovalent metal cations (e.g., $Na^{1+}$), monohydroxide metal bases (e.g., NaOH), and/or salts of monovalent metal cations (e.g., NaCl). The aqueous dispersion or solution can be applied in a variety of convention methods, including spray coating, roll coating, drop on demand printing, and dripping into a bulk solution. The polyvalent metal cations can cross-link the polysaccharide and cause the polysaccharide to gel.

The aqueous dispersion or solution of a therapeutic agent and a polysaccharide 16 can be applied to the surface of a stent in a single application process, or the therapeutic agent and the polysaccharide can be applied in a number of steps. For example, the therapeutic agent can be applied to the surface of the stent prior to applying the polysaccharide to the surface of the stent, and the aqueous dispersion or solution of a therapeutic agent and a polysaccharide 16 formed upon application of the polysaccharide. In some embodiments, the therapeutic agent could be applied and mixed with a polysaccharide on the surface of the stent after application of an aqueous solution of the polysaccharide to the surface, but before the polysaccharide has fully gelled.

By applying the aqueous dispersion or solution to the surface of the stent, polyvalent metal cations can be liberated from the surface of the stent. For example, the aqueous dispersion or solution can dissolve and/or oxidize the material of the surface of the stent to release the polyvalent metal cations. These cations then cross-link the polysaccharide. In some embodiments, the surface of the stent can include oxides, hydroxides, and/or salts that are capable of releasing polyvalent metal cations once exposed to the aqueous dispersion or solution. For example, the surface can include oxides and/or salts of Mg, Ca, Ba, Sr, Fe, Fe, Al, and/or Bi (e.g., MgO or $FeCl_3$). In some embodiments, the surface of the stent can include a metal or alloy that can erode and/or corrode to release polyvalent metal cations once exposed to the aqueous dispersion or solution. In some embodiments, the aqueous dispersion or solution can also include an oxidation accelerant. For example, metal chloride salts and peroxides can be used as oxidation accelerants. An oxidation accelerant can help to ensure that polyvalent cations are released from the surface of the medical implant.

The method can also include oxidizing the surface of the stent. For example, a magnesium stent 12 can be passivated to create a layer of MgO 14 on the surface of the stent prior to applying the aqueous dispersion or solution 16 to the surface of the stent. FIG. 2A depicts an example of a magnesium stent 12, with a MgO layer 14, and an applied aqueous dispersion or solution 16 prior to the ionization and diffusion of the $Mg^{2+}$ cations into the aqueous dispersion or solution 16. In some embodiments, the method can include the creation of salts on the surface of the stent. These processes can help facilitate release of polyvalent cations from the stent.

The polyvalent metal cations released from the stent cross-link the polysaccharide, forming an insoluble matrix. An example of the resulting coating 18 can be seen in FIG. 2B. The water in the polysaccharide matrix can be removed by applying heat and/or vacuum as needed. This process can be completely free of organic solvents. In some embodiments, the timing of the drying process, after the process of applying the aqueous dispersion or solution to the surface of the stent, can be used to control the thickness of the resulting coating.

Upon implantation of the stent within a body, the polysaccharide matrix 18 can release the therapeutic agent, e.g., by hydrating and solubilizing, and the bioerodible metal portion 12 can erode to release polyvalent metal cations capable of re-cross-linking the polysaccharide matrix. For example, the higher concentration of sodium and potassium ions in the blood stream can exchange with the polyvalent metal cations, allowing the coating to rehydrate and revert to a water soluble state. The erosion of the bioerodible metal portion 12 to release polyvalent metal cations, however, can re-cross-link the polysaccharide matrix. By controlling the relative concentration of polyvalent metal cations surrounding the stent 20, the rate of polysaccharide hydration and solubilization can be controlled. The rate of therapeutic agent release can also be controlled. Furthermore, the use of a polysaccharide drug eluting matrix with a bioerodible metal stent can create for a stent that completely erodes within a body.

Stent 20 can be of any desired shape and size (e.g., superficial femoral artery stents, coronary stents, aortic stents, peripheral vascular stents, gastrointestinal stents, urology stents, and neurology stents). Depending on the application, the stent can have a diameter of between, for example, 1 mm to 46 mm. In certain embodiments, a coronary stent can have an expanded diameter of from 2 mm to 6 mm. In some embodiments, a peripheral stent can have an expanded diameter of from 5 mm to 24 mm. In certain embodiments, a gastrointestinal and/or urology stent can have an expanded diameter of from 6 mm to about 30 mm. In some embodiments, a neurology stent can have an expanded diameter of from about 1 mm to about 12 mm. An Abdominal Aortic Aneurysm (AAA) stent and a Thoracic Aortic Aneurysm (TAA) stent can have a diameter from about 20 mm to about 46 mm.

In use, a stent can be used, e.g., delivered and expanded, using a catheter delivery system. Catheter systems are described in, for example, Wang U.S. Pat. No. 5,195,969, Hamlin U.S. Pat. No. 5,270,086, and Raeder-Devens, U.S. Pat. No. 6,726,712. Stents and stent delivery are also exemplified by the Sentinol® system, available from Boston Scientific Scimed, Maple Grove, Minn.

All publications, references, applications, and patents referred to herein are incorporated by reference in their entirety.

Other embodiments are within the scope of the claims.

What is claimed is:

1. A medical implant comprising: a bioerodable portion in the form of a stent, the bioerodable portion comprising (a) magnesium or a magnesium alloy and (b) MgO, and a coating overlying the bioerodable portion, wherein the coating comprises: i. a therapeutic agent, and ii. a polysaccharide matrix reversibly cross-linked with polyvalent metal cations, wherein implantation within a body, the therapeutic agents is released and the MgO ionizes to produce $Mg^{2+}$ cations, and the Mg or Mg alloy erodes to produce $Mg^{2+}$ cations, the $Mg^{2+}$ cations re-cross-link the polysaccharide matrix.

2. The medical implant of claim 1, wherein the polyvalent metal cations of the coating are $Mg^{2+}$.

3. The medical implant of claim 1, wherein polyvalent metal cations of the coating are selected from the group consisting of $Mg^{2+}$, $Zn^{2+}$, $Ca^{2+}$, $Ba^{2+}$, $Fe^{2+}$, $Fe^{3+}$, $Al^{3+}$, $Bi^{4+}$, and combinations thereof.

4. The medical implant of claim 1, wherein polyvalent metal cations of the coating are selected from the group consisting of oxides, hydroxides, and salts of elements selected from Groups IIA, IIIB, IVB, VB, VIB, VIIB, VIIIB, IB, and IIB of the periodic table or the group consisting of Al, Ga, In, Sn, Ti, and Bi.

5. The medical implant of claim 1, wherein the polyvalent cations in the matrix have a valence of 3 or greater.

6. The medical implant of claim 1, wherein the polysaccharide is selected from the group consisting of alginate, agar, gum Arabic, xanthan gum, dextran, gellan gum, pullulan, and combinations thereof.

7. The medical implant of claim 1, wherein the coating consists essentially of alginate cross-linked with polyvalent metal cations and the therapeutic agent.

8. A medical implant comprising: a bioerodable portion in the form of a stent, the bioerodable portion comprising (a) iron or an iron alloy and (b) $FeCl_3$, and a coating overlying the bioerodable portion, wherein the coating comprises: i. a therapeutic agent, and ii. a polysaccharide matrix reversibly cross-linked with polyvalent metal cations, wherein implantation within a blood stream of a body, sodium or potassium ions in the blood stream exchange with the polyvalent metal cations cross-linking the polysaccharide matrix, the $FeCl_3$ ionizes to release $Fe^{3+}$ cations and the iron or iron alloy erodes to release $Fe^{2+}$ cations, $Fe^{3+}$ cations, or a combination thereof, wherein the $Fe^{2+}$ cations, $Fe^{3+}$ cations, or a combination thereof re-cross-link the polysaccharide matrix to control the rate of polysaccharide hydration and solubilization and thus control a rate of therapeutic agent release wherein upon implantation within a body, the therapeutic agent is released and the $FeCl_3$ ionizes to produce $Fe^{3+}$ cations, and the iron or iron alloy erodes to produce $Fe^{2+}$ cations, $Fe^{3+}$ cations, or a combination thereof, the $Fe^{2+}$ cations, $Fe^{3+}$ cations, or a combination thereof, re-cross-link the polysaccharide matrix.

9. The medical implant of claim 8, wherein polyvalent metal cations of the coating are selected from the group consisting of $Mg^{2+}$, $Zn^{2+}$, $Ca^{2+}$, $Ba^{2+}$, $Fe^{2+}$, $Fe^{3+}$, $Al^{3+}$, $Bi^{4+}$, and combinations thereof.

10. The medical implant of claim 8, wherein the polyvalent cations in the matrix have a valence of 3 or greater.

11. The medical implant of claim 9, wherein the polysaccharide is selected from the group consisting of alginate, agar, gum Arabic, xanthan gum, dextran, gellan gum, pullulan, and combinations thereof.

12. The medical implant of claim 8, wherein the coating consists essentially of alginate cross-linked with polyvalent metal cations and the therapeutic agent.

* * * * *

UNITED STATES PATENT AND TRADEMARK OFFICE
CERTIFICATE OF CORRECTION

PATENT NO. : 7,939,096 B2  
APPLICATION NO. : 12/369397  
DATED : May 10, 2011  
INVENTOR(S) : Geoffrey Wilson Page 1 of 1

It is certified that error appears in the above-identified patent and that said Letters Patent is hereby corrected as shown below:

Column 9, Claim 1, Line 7: delete "bioerodable" and insert --bioerodible--.

Column 9, Claim 1, Line 9: delete "bioerodable" and insert --bioerodible--.

Column 10, Claim 8, Line 2: delete "bioerodable" and insert --bioerodible--.

Signed and Sealed this
Fourth Day of October, 2011

David J. Kappos
*Director of the United States Patent and Trademark Office*